United States Patent
Kiely et al.

(10) Patent No.: US 11,352,272 B2
(45) Date of Patent: Jun. 7, 2022

(54) BIO-ELECTROCHEMICAL SENSOR AND METHOD FOR OPTIMIZING PERFORMANCE OF A WASTEWATER TREATMENT SYSTEM

(71) Applicant: SENTRY: WATER MONITORING AND CONTROL INC., Charlottetown (CA)

(72) Inventors: Patrick Desmond Kiely, Gatineau (CA); Monica Cella, Kelowna (CA); Jack Ambler, Conshohocken, PA (US); Rebecca Connolly, Stratford (CA)

(73) Assignee: SENTRY:WATER MONITORING AND CONTROL INC., Charlottetown (CA)

( * ) Notice: Subject to any disclaimer, the term of this patent is extended or adjusted under 35 U.S.C. 154(b) by 446 days.

(21) Appl. No.: 16/463,751

(22) PCT Filed: Nov. 27, 2017

(86) PCT No.: PCT/CA2017/051425
§ 371 (c)(1),
(2) Date: May 23, 2019

(87) PCT Pub. No.: WO2018/094537
PCT Pub. Date: May 31, 2018

(65) Prior Publication Data
US 2019/0389751 A1 Dec. 26, 2019

Related U.S. Application Data

(60) Provisional application No. 62/426,394, filed on Nov. 25, 2016.

(51) Int. Cl.
*G01N 33/18* (2006.01)
*C02F 3/28* (2006.01)
(Continued)

(52) U.S. Cl.
CPC .......... *C02F 1/5245* (2013.01); *C02F 3/2853* (2013.01); *G01N 33/1806* (2013.01);
(Continued)

(58) Field of Classification Search
CPC ............ C02F 2209/00; C02F 2209/003; C02F 2209/08; C02F 2209/03; C02F 1/5236;
(Continued)

(56) References Cited

U.S. PATENT DOCUMENTS 5,013,442 A   5/1991  Davis et al.
5,466,604 A   11/1995 Yang et al.
(Continued)

FOREIGN PATENT DOCUMENTS

CA    2838737 A1   12/2012
EP    2595924 A1    5/2013
(Continued)

OTHER PUBLICATIONS

Xu et al. Biosensors and Bioelectronics, 85, 2016, 232 (Year: 2016).*
(Continued)

*Primary Examiner* — Gurpreet Kaur
(74) *Attorney, Agent, or Firm* — Borden Ladner Gervais LLP; Michael Damiani

(57) ABSTRACT

The present disclosure generally relates to a system for monitoring and/or controlling one or more agents, such as cleaning agents, in a wastewater treatment system. The system comprises a bio-electrochemical sensor for monitoring metabolic activity of a population of exo-electrogenic bacteria and providing an electrical output corresponding with the metabolic activity, where the bio-electrochemical sensor comprises an electrode pair and a power source for delivering a voltage across the electrode pair, and an electrical output analyzer for analyzing the electrical output and
(Continued)

correlating the electrical output with the one or more agents in the wastewater treatment system. a change in electrical output beyond a threshold indicates that an adjustment in the delivery of the one or more agents is needed. a method and sensor for monitoring and/or controlling a cleaning process in a wastewater treatment system are also provided. The system, method, and sensor disclosed herein are particularly useful for cleaning membranes incorporated in a wastewater treatment process.

19 Claims, 11 Drawing Sheets

(51) Int. Cl.
  *C02F 1/52* (2006.01)
  *C02F 3/00* (2006.01)
(52) U.S. Cl.
  CPC .......... *C02F 3/005* (2013.01); *C02F 2209/03* (2013.01); *C02F 2303/16* (2013.01); *G01N 33/1886* (2013.01)
(58) Field of Classification Search
  CPC ...... C02F 1/5245; C02F 3/005; C02F 3/2853; C02F 2305/00; C02F 2303/04; C02F 2303/185; G01N 33/1886; C12M 1/34
  See application file for complete search history.

(56) References Cited

U.S. PATENT DOCUMENTS

| | | | |
|---|---|---|---|
| 5,494,588 A | 2/1996 | Lazonby | |
| 5,792,342 A | 8/1998 | Heller et al. | |
| 6,161,435 A | 12/2000 | Bond et al. | |
| 6,458,257 B1 | 10/2002 | Andrews et al. | |
| 6,699,684 B2 | 3/2004 | Ho et al. | |
| 6,805,806 B2 | 10/2004 | Arnaud | |
| 7,439,047 B2 | 10/2008 | Rozendal et al. | |
| 7,906,008 B2 | 3/2011 | Kumar et al. | |
| 8,192,854 B2 | 6/2012 | Borole | |
| 8,440,438 B2 | 5/2013 | Cheng et al. | |
| 9,046,478 B2 | 6/2015 | Buck et al. | |
| 9,309,138 B2 | 4/2016 | Ogiwara et al. | |
| 2004/0007525 A1 | 1/2004 | Rabie et al. | |
| 2008/0220292 A1 | 9/2008 | Rabaey et al. | |
| 2010/0119920 A1 | 5/2010 | Logan et al. | |
| 2010/0151279 A1 | 6/2010 | Logan et al. | |
| 2010/0200495 A1 | 8/2010 | Borole et al. | |
| 2010/0297737 A1 | 11/2010 | Barkeloo et al. | |
| 2011/0236769 A1 | 9/2011 | Xie et al. | |
| 2012/0231492 A1 | 9/2012 | Bitterly et al. | |
| 2013/0001142 A1* | 1/2013 | Novak | C02F 3/1268 210/96.2 |
| 2013/0017414 A1 | 1/2013 | He | |
| 2014/0048424 A1 | 2/2014 | Gu | |
| 2014/0069806 A1 | 3/2014 | Silver et al. | |
| 2014/0353170 A1 | 12/2014 | Huang et al. | |

FOREIGN PATENT DOCUMENTS

| | | |
|---|---|---|
| KR | 101566085 B1 | 11/2015 |
| WO | 2011150473 A1 | 12/2011 |
| WO | 2012012647 A2 | 1/2012 |
| WO | 2012173988 A1 | 12/2012 |
| WO | 2014172791 A1 | 10/2014 |

OTHER PUBLICATIONS

European Patent Application No. 17873104.8, Extended European Search Report dated Jul. 27, 2020.
U.S. Appl. No. 14/126,264, Final Office Action dated Sep. 25, 2017.
U.S. Appl. No. 14/126,264, Non-Final Office Action dated Dec. 22, 2017.
U.S. Appl. No. 14/126,264, Non-Final Office Action dated Mar. 10, 2017.
U.S. Appl. No. 14/126,264, Non-Final Office Action dated Apr. 2, 2019.
U.S. Appl. No. 14/126,264, Non-Final Office Action dated Sep. 14, 2018.
International Patent Application No. PCT/CA2017/051425, International Preliminary Report of Patentability dated Feb. 22, 2019.
International Patent Application No. PCT/CA2017/051425, International Search Report and Written Opinion dated Feb. 26, 2018.
Zhang et al., "A Potentiometric Flow Biosensor Based on Ammonia-Oxidizing Bacteria for the Detection of Toxicity in Water", Sensors, May 2013, vol. 13(6), pp. 6937-6945, ISSN 1424-8220.

* cited by examiner

BIO-ELECTROCHEMICAL SENSOR AND METHOD FOR OPTIMIZING PERFORMANCE OF A WASTEWATER TREATMENT SYSTEM

FIELD

The present disclosure relates to a system for detecting and reducing system imbalances in wastewater treatment systems, and methods and sensors related thereto.

BACKGROUND

The necessity of cost-efficient and reliable wastewater treatment processes has increased in order to meet more stringent environmental regulations and increased system reliability requirements; and, to allow operators to reduce costs associated with system operation and maintenance.

Membrane-based wastewater treatment systems (MBR) are used in wastewater treatment processes where a perm-selective membrane, e.g. microfiltration or ultrafiltration membrane, is integrated with a biological process, for example anaerobic digestion. These processes utilize membranes that treat wastewater by passing the wastewater through pores in the membrane under pressure, or by passing the wastewater through the pores by gravity. Examples include nanofiltration, microfiltration, and ultrafiltration, among others. The pores on these membranes are clogged over time by excessive biofilm growth, extracellular biomass, precipitates, etc., which may collectively be referred to as "debris". This debris impedes the flow of wastewater and reduces the effectiveness of the membranes.

The industry standard to address this issue is to periodically dose the wastewater treatment system with cleaning agents that break down debris and unclog the membrane pores. The microbiology used to primarily treat the wastewater contaminants are comprised of "flocs" or granular microbial communities that are suspended in the liquid. When the cleaning agents are added to the wastewater treatment systems they can cause system imbalances, for example, by negatively impacting the suspended microbiology, which in turn results in reduced performance of the wastewater treatment system.

Furthermore, wastewater treatment system equipment located upstream of the biological process requires periodic cleaning. In some instances, residual cleaning agents from upstream cleaning may be carried into a reactor in the wastewater stream and cause system imbalances.

Improvements in detecting and reducing system imbalances in wastewater treatment systems are desirable.

SUMMARY

Strategies to address the negative effects of cleaning agents in wastewater treatment systems include: (1) membrane-based technologies that isolate the cleaning agents from the biological process; (2) decreasing the amount of cleaning agent; and (3) sensor technologies that requires an aerobic environment. These strategies can require: (1) costly equipment, for example when an additional step of removing waste streams is introduced, which requires expensive pumping and hauling, or an additional step of sample removal for testing is introduced, which requires expensive system retrofitting; (2) under-dosing systems that result in an increased frequency of cleaning and therefore costly down time of the wastewater treatment system; or (3) a combination thereof.

The present disclosure describes a system that monitors the effects of one or more agents in a wastewater treatment system in real time without a need for oxygen terminal electron acceptors, and, can cause the wastewater treatment system to adjust the delivery of the one or more agents when needed. As used herein, the phrase "oxygen terminal electron acceptors" refers to use of the compound dioxygen (i.e., $O_2$) as a terminal electron acceptor. In contrast, the phrase "non-oxygen terminal electron acceptors" refers to terminal electron acceptors that are not dioxygen (i.e., $O_2$); however, this is not meant to exclude terminal electron acceptors that may be comprised of oxygen atoms, such as but not limited to $CO_2$, etc.

The present disclosure provides a system for monitoring, and/or controlling the delivery of, one or more agents in a wastewater treatment system. Generally, the system comprises a bio-electrochemical sensor for monitoring in real time the effects of the one or more agents and, with an input of power, providing a corresponding electrical output; and an electrical output analyzer for analyzing the electrical output and adjusting the system, if needed. The present disclosure also provides for a method of monitoring, and/or controlling the delivery of, one or more agents in a wastewater treatment system. Generally, the method comprises: applying power to a sensor and measuring the electrical output of the sensor, where the electric output correlates with the one or more agents in the system in real time; and, causing the system to adjust, if needed. The present disclosure also describes sensors that may be used in the above described system as well as to perform the above described method.

Exemplary systems, methods, and sensors may: (1) reduce the cost of operation; (2) decrease amount of costly equipment; (3) increase efficiency and/or performance of the wastewater treatment system (4) increase accuracy of measurements; or (5) a combination thereof, in comparison to systems, methods, and sensors that require oxygen terminal electron acceptors to operate, by, for example: (1) decreasing the size of the bio-electrochemical sensor; (2) decreasing the downtime of wastewater treatment systems by adjusting the amount, type, or combination thereof, of cleaning agents delivered into the wastewater treatment system; or (3) a combination thereof.

In one aspect, the present disclosure provides for a system for monitoring one or more agents in a wastewater treatment system. The system comprises: a bio-electrochemical sensor for monitoring metabolic activity of a population of exoelectrogenic bacteria and providing an electrical output corresponding with the metabolic activity, the bio-electrochemical sensor comprising an electrode pair and a power source for delivering a voltage across the electrode pair; and an electrical output analyzer for analyzing the electrical output and correlating the electrical output with the one or more agents in the wastewater treatment system. The wastewater treatment system may be an anaerobic digestion system, and the bio-electrochemical sensor may be located within the anaerobic digestion system. The anaerobic digestion system may incorporate a treatment process comprising a membrane.

The one or more agents may comprise at least one cleaning agent. The at least one cleaning agent may be a membrane cleaning agent. The at least one cleaning agent may comprise sodium hypochlorite, peracetic acid, citric acid, or a combination thereof. The at least one cleaning agent may comprise peracetic acid.

The herein described systems may further comprise a controller in communication with the electrical output analyzer for initiating a cleaning process in response to a trigger. The herein described systems may further comprise a pressure sensor in communication with the controller for measuring wastewater pressure across the membrane, where the trigger is a change in the pressure. The herein described systems may also further comprise a flow meter in communication with the controller for measuring wastewater flow rate across the membrane, where the trigger is a change in the flow rate. The trigger may also be a pre-determined time.

The present disclosure also provides a system for controlling the delivery of one or more agents to a wastewater treatment system. The system comprises: a bio-electrochemical sensor for monitoring metabolic activity of a population of exo-electrogenic bacteria and providing an electrical output correlating with the metabolic activity, the bio-electrochemical sensor comprising an electrode pair and a power source for delivering a voltage across the electrode pair; an electrical output analyzer for analyzing the electrical output and providing a signal to a controller; and a pump operably coupled to the controller for controlling the delivery of the one or more agents in response to the signal. The wastewater treatment system may be an anaerobic digestion system, and the bio-electrochemical sensor may be located within the anaerobic digestion system. The anaerobic digestion system may incorporate a treatment process comprising a membrane. The herein described systems may permit real time adjustments in the delivery of the one or more agents throughout a membrane cleaning process.

The one or more agents may comprise at least one cleaning agent. The at least one cleaning agent may be a membrane cleaning agent. The at least one cleaning agent may comprise sodium hypochlorite, peracetic acid, citric acid, or a combination thereof. The at least one cleaning agent may comprise peracetic acid.

A change in electrical output beyond a threshold may produce a signal to adjust the delivery of the one or more agents. The threshold may be a deviation of greater than about 10% from an operating electrical output. The change in electrical output may be monitored over a period of time.

The present disclosure further provides a system for controlling the delivery of one or more agents to a wastewater treatment system. The system comprises: a bio-electrochemical sensor for monitoring metabolic activity of a population of exo-electrogenic bacteria and providing an electrical output correlating with the metabolic activity, the bio-electrochemical sensor comprising an electrode pair and a power source for delivering a voltage across the electrode pair; an electrical output analyzer for analyzing the electrical output and providing a signal to a controller; and a valve operably coupled to the controller for controlling the delivery of wastewater into the wastewater treatment system in response to the signal. The wastewater treatment system may be an anaerobic digestion system, and the bio-electrochemical sensor may be located within the anaerobic digestion system. The anaerobic digestion system may incorporate a treatment process comprising a membrane.

The one or more agents may comprise at least one cleaning agent. The at least one cleaning agent may be a wastewater treatment system equipment cleaning agent.

The electrode pair of the herein described systems may comprise an anode and a cathode, the anode in electrical communication with the exo-electrogenic bacteria for receiving electrons therefrom; and the herein described bio-electrochemical sensors may further comprise a current sensor for measuring electron flow between the anode and the cathode and producing an electrical output that correlates with metabolic activity of the exo-electrogenic bacteria. The current sensor may comprise a terminal electron acceptor in electrical communication with the cathode for receiving electrons therefrom, and a resistor in electrical communication with the terminal electron acceptor, where an electric current is measured across the resistor. The terminal electron accepter may be a non-oxygen electron acceptor. The non-oxygen electron acceptor may be H+ or $CO_2$.

In another aspect, the present disclosure provides a method of monitoring one or more agents in a wastewater treatment system. The method comprises: applying power to a bio-electrochemical sensor; measuring an electrical output of the bio-electrochemical sensor and correlating the output with metabolic activity of exo-electrogenic bacteria present in the system; and correlating the electrical output with the one or more agents in the wastewater treatment system. The wastewater treatment system may be an anaerobic digestion system. The step of measuring the electrical output may be measured within the anaerobic digestion system.

The herein described methods may be incorporated in a method of cleaning a membrane associated with the wastewater treatment process. The herein described methods may further comprise initiating a membrane cleaning cycle in response to a trigger. The trigger may be a change in the wastewater pressure across the membrane. The trigger may also be a change in the wastewater flow rate across the membrane. The trigger may be a pre-determined time.

The present disclosure also provides a method of controlling the delivery of one or more agents in a wastewater treatment system. The method comprises: applying power to a bio-electrochemical sensor; measuring an electrical output of the bio-electrochemical sensor and correlating the output with metabolic activity of exo-electrogenic bacteria present in the system; delivering the one or more agents into the system; monitoring a change in the electrical output in response to the one or more agents; and adjusting the delivery of the one or more agents in response to a change in the electrical output. The wastewater treatment system may be an anaerobic digestion system. The step of measuring the electrical output may be measured within the anaerobic digestion system.

Real time adjustments in the delivery of the one or more agents may be made throughout a cleaning process in response to changes in the electrical output. The herein described methods may be incorporated in a method of cleaning a membrane associated with the wastewater treatment process. The herein described methods may further comprise correlating the electrical output with wastewater pressure across the membrane. The herein described methods may further comprise correlating the electrical output with wastewater flow rate across the membrane. Adjusting the delivery of the one or more agents may be made in response to a change in electrical output beyond a threshold. The threshold may be a deviation of greater than about 10% from an operating electrical output. The change in electrical output may be monitored over a period of time.

The one or more agents may comprise at least one cleaning agent. The at least one cleaning agent may be a membrane cleaning agent. The at least one cleaning agent may comprise sodium hypochlorite, peracetic acid, citric acid, or a combination thereof. The at least one cleaning agent may comprise peracetic acid.

In yet another aspect, the present disclosure provides a bio-electrochemical sensor for monitoring metabolic activity of a population of exo-electrogenic bacteria in response to one or more agents delivered to a wastewater treatment system. The sensor comprises: an electrode pair comprising an anode and a cathode, the anode in electrical communication with the exo-electrogenic bacteria for receiving electrons therefrom; a current sensor for measuring electron flow between the anode and the cathode and producing an electrical output that correlates with metabolic activity of the exo-electrogenic bacteria; and a power source in electrical communication with the electrode pair for delivering a voltage across the electrode pair.

The one or more agents may comprise at least one cleaning agent. The at least one cleaning agent may be a membrane cleaning agent. The at least one cleaning agent may be a wastewater treatment system equipment cleaning agent. The at least one cleaning agent may comprise sodium hypochlorite, peracetic acid, citric acid, or a combination thereof. The at least one cleaning agent may comprise peracetic acid.

The wastewater treatment system may be an anaerobic digestion system. The anaerobic digestion system may incorporate a treatment process comprising a membrane.

The herein described sensors may comprise a terminal electron acceptor in electrical communication with the cathode for receiving electrons therefrom, and a resistor in electrical communication with the terminal electron acceptor, wherein electric current is measured across the resistor.

The present disclosure also provides a bio-electrochemical sensor for monitoring metabolic activity of a population of exo-electrogenic bacteria in response to one or more agents delivered to a wastewater treatment system. The sensor comprises: a support comprising a bio support material for supporting the growth of exo-electrogenic bacteria; at least one electrode pair connected to the support, the at least one electrode pair comprising an anode and a cathode, where the exo-electrogenic bacteria are in proximity to the anode and release electrons to the anode, the released electrons flowing from the anode to the cathode; a power source in electrical communication with the electrode pair for delivering a voltage across the electrode pair; a terminal electron acceptor electrically coupled to the cathode for receiving electrons from the cathode and for generating an electrical output that correlates with metabolic activity of the exo-electrogenic bacteria; and a resistor electrically coupled to the terminal electron acceptor, wherein the output is measured across the resistor, using a data acquisition system.

The herein described sensors may have a terminal electron accepter that is a non-oxygen electron acceptor. The non-oxygen electron acceptor may be H+ or $CO_2$.

The anode and the cathode of the herein described sensors may be configured in parallel, and at least a portion of the anode overlaps with at least a portion of the cathode, and where the distance between the overlapping portions is about 3 mm.

The anode may be coupled to a bio support material capable of sustaining growth of the exo-electrogenic bacteria. The exo-electrogenic bacteria may comprise one or more of *Geobacter sulfurreducens*, *Geobacter metaloreducens*, *Pseudomonas aeruginosa*, *Shewanella putrefaciens*. The exo-electrogenic bacteria may comprise *Geobacter sulfurreducens*.

The herein described sensors may be used for monitoring metabolic activity of exo-electrogenic bacteria during cleaning of a membrane in a wastewater treatment system such that delivery of one or more cleaning agents can be adjusted, as needed, during the cleaning process in response to changes in the metabolic activity. The herein described sensors may also be used for monitoring metabolic activity of exo-electrogenic bacteria during anaerobic digestion such that delivery of wastewater into the anaerobic digester can be adjusted, as needed, during anaerobic digestion in response to changes in the metabolic activity.

The present disclosure also provides for herein described systems where the sensor is a herein described bio-electrochemical sensor. The present disclosure further provides for a method of controlling the delivery of one or more agents in a wastewater treatment system. The method comprises: measuring an electrical output of a herein described bio-electrochemical sensor, and correlating the output with metabolic activity of exo-electrogenic bacteria present in the system; delivering the one or more agents into the system; monitoring a change in the electrical output in response to the one or more agents; and adjusting the delivery of the one or more agents in response to a change in the electrical output. The wastewater treatment system may be an anaerobic digestion system.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of examples only, with reference to the attached Figures.

DETAILED DESCRIPTION

Figure 1:
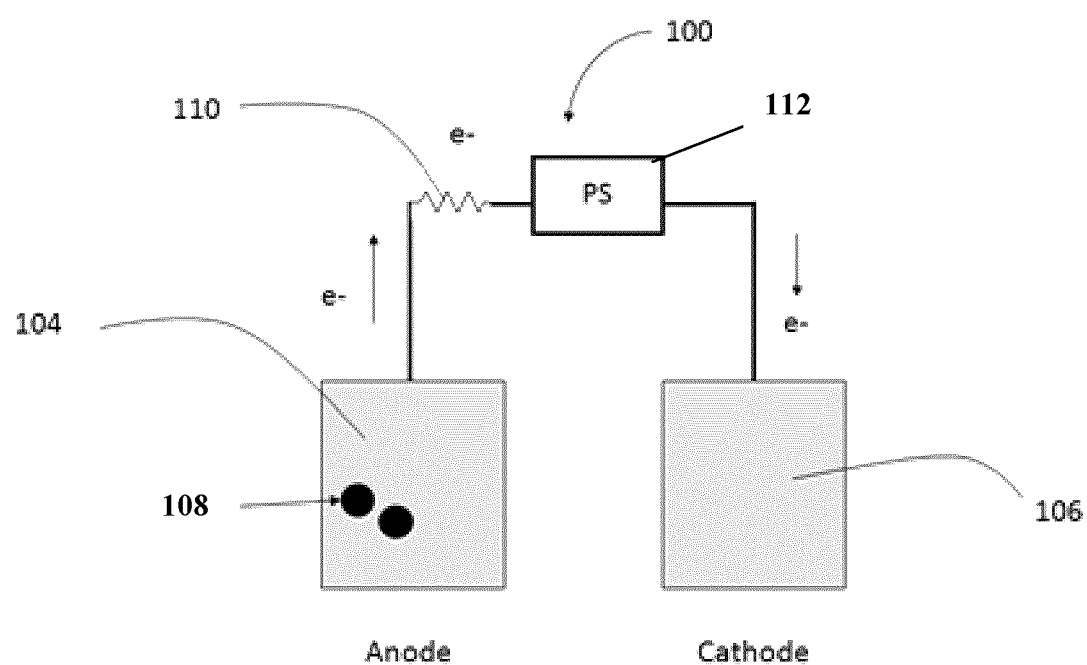
FIG. 1 is an illustration of an exemplary bio-electrochemical sensor according to the present disclosure.

Generally, the present discourse provides a system for monitoring one or more agents in a wastewater treatment system. The system comprises: a bio-electrochemical sensor for monitoring metabolic activity of a population of exo-electrogenic bacteria and providing an electrical output corresponding with the metabolic activity, the bio-electrochemical sensor comprising an electrode pair and a power source for delivering a voltage across the electrode pair; and an electrical output analyzer for analyzing the electrical output and correlating the electrical output with the one or more agents in the wastewater treatment system. In some examples according to the present disclosure, the system further provides a signal based on the electrical output resulting from a change in the metabolic activity of the population of exo-electrogenic bacteria, where the signal can trigger an adjustment of the system, for example, to initiate, discontinue, increase, and/or decrease delivery of one or more agents into the wastewater treatment system. The adjustment of the wastewater treatment system may be performed by an operator in response to the signal, or may be performed by an automated device or process.

The present disclosure also provides a system for controlling the delivery of one or more agents to a wastewater treatment system. The system comprises: a bio-electrochemical sensor for monitoring metabolic activity of a population of exo-electrogenic bacteria and providing an electrical output correlating with the metabolic activity, the bio-electrochemical sensor comprising an electrode pair and a power source for delivering a voltage across the electrode pair; an electrical output analyzer for analyzing the electrical output and providing a signal to a controller; and a pump operably coupled to the controller for controlling the delivery of the one or more agents in response to the signal. In another example, the present disclosure provides a system for controlling the delivery of one or more agents to a wastewater treatment system. The system comprises: a bio-electrochemical sensor for monitoring metabolic activity of a population of exo-electrogenic bacteria and providing an electrical output correlating with the metabolic activity, the bio-electrochemical sensor comprising an electrode pair and a power source for delivering a voltage across the electrode pair; an electrical output analyzer for analyzing the electrical output and providing a signal to a controller; and a valve operably coupled to the controller for controlling the delivery of wastewater into the wastewater treatment system in response to the signal.

The present disclosure also provides a method of monitoring one or more agents in a wastewater treatment system. The method comprises: applying power to a bio-electrochemical sensor; measuring an electrical output of the bio-electrochemical sensor and correlating the output with metabolic activity of exo-electrogenic bacteria present in the wastewater treatment system; and correlating the electrical output with the one or more agents in the wastewater treatment system. In some examples according to the present disclosure, the method further comprises monitoring a change in the metabolic activity, and adjusting the wastewater treatment system, for example, to initiate, discontinue, increase, and/or decrease the delivery of one or more agents into the wastewater treatment system. For example, the present disclosure provides a method of controlling the delivery of one or more agents in a wastewater treatment system. The method comprises: applying power to a bio-electrochemical sensor; measuring an electrical output of the bio-electrochemical sensor and correlating the output with metabolic activity of exo-electrogenic bacteria present in the wastewater treatment system; delivering the one or more agents into the system; monitoring a change in the electrical output in response to the one or more agents; and adjusting the delivery of the one or more agents in response to a change in the electrical output.

In the context of the present disclosure, the wastewater treatment system includes any wastewater treatment system that converts wastewater into an effluent that can either be discharged, returned to a water cycle, or reused. In some examples according to the present disclosure, the wastewater treatment process involves anaerobic digestion, for example, an anaerobic suspended growth digestion system, in which microbes break down biodegradable material or contaminants in the absence of oxygen. In some examples according to the present disclosure, the wastewater treatment system is a membrane-based treatment system (MBR), for example a membrane-based anaerobic digestion system. Exemplary systems may employ one or more membranes. In multiple membrane examples, the membranes may be arranged in parallel or in series. The membranes may be any suitable shape, for example, flat, tubular or a combination thereof. The membranes may be any suitable material or porosity as may be determined by a skilled person.

In the context of the present disclosure, the bio-electrochemical sensor is any sensor that can, with a voltage input, monitor the metabolic activity of microbes in a wastewater treatment system in real time, and provide an electrical output that correlates with the metabolic activity.

Without being bound by theory, bio-electrochemical sensors according to the present disclosure produce a substantially constant current under constant wastewater treatment system conditions. This may, for example, be referred to as a steady-state current. Once steady-state is reached in the wastewater treatment system, a deviation indicates an impact on the metabolic activity of the resident microbes. For example, when a toxic component is introduced into the wastewater treatment system or the wastewater treatment system is imbalanced, the metabolic activity of the microorganism community in the wastewater treatment system can be impacted, resulting in a deviation from a reference current or steady-state current. A system operator will be able to determine a threshold deviation or threshold current at which an action is needed.

The present disclosure also provides for a bio-electrochemical sensor for monitoring metabolic activity of a population of exo-electrogenic bacteria in response to one or more agents delivered to a wastewater treatment system. The sensor comprises: an electrode pair comprising an anode and a cathode, the anode in electrical communication with the exo-electrogenic bacteria for receiving electrons therefrom; a current sensor for measuring electron flow between the anode and the cathode and producing an electrical output that correlates with metabolic activity of the exo-electrogenic bacteria; and a power source in electrical communication with the electrode pair for delivering a voltage across the electrode pair. In some examples according to the present disclosure, the bio-electrochemical sensor for monitoring metabolic activity of a population of exo-electrogenic bacteria in response to one or more agents delivered to a wastewater treatment system comprises: a support comprising a bio support material for supporting growth of exo-electrogenic bacteria; at least one electrode pair connected to the support, the at least one electrode pair comprising an anode and a cathode, where the exo-electrogenic bacteria are in proximity to the anode and release electrons to the anode, the released electrons flowing from the anode to the cathode; a power source in electrical communication with the electrode pair for delivering a voltage across the electrode pair; a terminal electron acceptor electrically coupled to the cathode for receiving electrons from the cathode and for generating an electrical output that correlates with metabolic activity of the exo-electrogenic bacteria; and a resistor electrically coupled to the terminal electron acceptor, wherein the output is measured across the resistor, using a data acquisition system or electrical output analyzer.

In the context of the present disclosure, a bio support material is any material that can support growth of exo-electrogenic bacteria. In some examples, the bio support material is a metallic compound or alloy, a stainless steel compound or alloy, a carbon based compound or alloy, or a combination thereof. In some preferred examples, the bio support is a corrosion resistant metallic compound or alloy, for example, stainless steel 316. In some examples according to the present disclosure, the exo-electrogenic bacteria are fixed directly to the bio support material. Alternatively, the exo-electrogenic bacteria are fixed to an intermediate component that is in electrical communication with the bio support material and the exo-electrogenic bacteria. In other examples, the exo-electrogenic bacteria are detachable from the bio support material. The exo-electrogenic bacteria may also be grown on the bio support material.

In the context of the present disclosure, it should be understood that reference to "microbe", "microorganism" or "bacteria" includes one or more bacterium. Typically, a wastewater treatment system will comprise more than one type of resident bacteria. The terms "microbe and "microorganism" are used interchangeably herein to describe the one or more resident bacterium in the wastewater treatment system. The terms "electrogenic" and "exo-electrogenic" bacteria are used interchangeably herein.

In the context of the present disclosure, metabolic activity refers to any reaction between the exo-electrogenic bacteria and at least one component in the wastewater treatment system that causes an electron to transfer from the exo-electrogenic bacteria to the bio-electrochemical sensor. In the context of the present disclosure, exo-electrogenic bacteria includes any bacteria that has the ability to transfer electrons extracellularly, and that is metabolically activatable by at least one component in the wastewater treatment system. In some examples according to the present disclosure, metabolically activated refers to the anaerobic digestion of wastewater components, such as volatile fatty acids, organic acids, and complex organic compounds resulting in the production of electrons. In some examples, the digestion may include processes such as hydrolysis, acidogenesis, acetogenesis, and methanogenesis.

In some examples according to the present disclosure, the exo-electrogenic bacteria include one of more of *Geobacter sulfurreducens, Geobacter metaloreducens, Pseudomonas aeruginosa*, and *Shewanella putrefaciens*. The number and type of exo-electrogenic bacteria may depend on the type of wastewater stream. In some preferred examples, the exo-electrogenic bacteria include *Geobacter sulfurreducens*.

In the context of the present disclosure, measuring the current generated by the exo-electrogenic bacteria is performed by a sensor that is capable of converting chemical energy into electricity, for example, a bio-electrochemical sensor. In accordance with the present disclosure, the bio-electrochemical sensor is in electrical communication with the exo-electrogenic bacteria and a terminal electron acceptor. In some examples according to the present disclosure, the sensor comprises at least one electrode pair comprising an anode and a cathode. In some examples, the anode of the one electrode pair is in direct electrical communication with exo-electrogenic bacteria, for example, the exo-electrogenic bacteria may be attached to, grown on, or otherwise electrically coupled with, the anode. In other examples, the sensor is in indirect electrical communication with the exo-electrogenic bacteria, for example, but incorporating an electrical linker between the exo-electrogenic bacteria and the sensor.

In accordance with the present disclosure, exo-electrogenic bacteria function by oxidizing wastewater components and transferring electrons extracellularly to an electrode surface. The rate at which electrons are transferred to the electrode correlates with the metabolic activity of the exo-electrogenic bacteria or biofilm. The exo-electrogenic bacteria generally reflect the population of microbes suspended in the wastewater treatment system. The data produced directly from the bio-electrochemical sensor can thus be used to monitor the metabolic activity of the microbes to indicate events, such as toxic events and system imbalances, affecting the resident microbiology in the wastewater treatment system. The bio-electrochemical sensor can allow for real-time communication between wastewater treatment bacteria or biofilms and the operational control of the wastewater treatment system. This information can be used to control, adjust and/or optimize wastewater treatment system performance in real-time.

In the context of the present disclosure, the terms "electrical communication" or "electrically coupled" mean that electrons are transferable between the recited components. In some examples according to the present disclosure, components that are in "electrical communication" or are "electrically coupled" are connected by an electrical wire.

In some examples according to the present disclosure, the bio-electrochemical sensor comprises a power source in electrical communication with the electrode pair, for example when operating the bio-electrochemical sensor in an anaerobic environment is preferable. The power source may be any power-emitting instrument that applies a voltage across the electrode pair of the bio-electrochemical sensor. In some examples according to the present disclosure, the applied voltage is from about 0.1 V to about 1.5 V, for example, about 0.1 V; 0.2 V, 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V; or the voltage is between any one of the voltages listed above to any other of the voltages listed above. In some examples according to the present disclosure, the applied voltage is from about 0.3 V to about 0.9 V. Without being bound by theory, the applied voltage to the bio-electrochemical sensor may allow the sensor to utilize a non-oxygen terminal electron acceptor, for example, $H^+$ or $CO_2$. In the context of the present disclosure, a terminal electron acceptor refers to any component that receives or accepts an electron. In some examples, the terminal electron accepter is any conductive material that allows for an electrochemical reduction reaction, for example, the reduction of $H^+$ as a terminal electron acceptor in the production of hydrogen gas.

Operating the herein described systems, methods and bio-electrochemical sensors in an anaerobic environment may: (1) decrease amount of costly equipment; (2) increase efficiency of the wastewater treatment system; (3) increase accuracy of the correlation of the electrical output and the metabolic activity of the exo-electrogenic bacteria; or (4) a combination thereof, in comparison to systems, methods, and sensors that require oxygen terminal electron acceptors to operate. In some examples of the present disclosure, the bio-electrochemical sensor may be configured into a compact design, for example, by configuring the anode and cathode of the sensor in close proximity to one another. This compact design may allow the sensor to be immersed entirely into an anaerobic environment, positioned within an anaerobic chamber in areas suitable for increasing accuracy of measurement, or a combination thereof. For example, in some membrane-based treatment systems, positioning the sensor in close proximity to a membrane may allow for a more accurate measurement of the effect of system imbalances on the membrane. The compact design and ability to be immersed into an anaerobic environment may also decrease the amount of equipment required to use the bio-electrochemical sensor in a wastewater treatment system; for example, by: (1) decreasing equipment that would otherwise be required to retrofit existing wastewater treatment systems to couple with an aerobic sensor; (2) decreasing equipment required to enable aerobic sensors to be in electrical communication with oxygen terminal electron acceptors; or (3) a combination thereof.

In the context of the present disclosure, "immersed" within or into an environment refers to wholly sinking the bio-electrochemical sensor within the environment. In some examples according to the present disclosure, a portion of the bio-electrochemical sensor is immersed into an anaerobic wastewater treatment environment, for example, about 10%, about 25%, about 50%, about 75%, about 80%, about 85%, about 90%, about 95%, 100%, or the percentage is from any one of the percentages listed above to any other of the percentages listed above, of the surface area of a bio-electrochemical sensor is immersed into an anaerobic wastewater treatment environment. In some examples according to the present disclosure, 100% of the surface area of the bio-electrochemical sensor is immersed into an anaerobic wastewater treatment environment, for example when increasing the accuracy of monitoring one or more agents in the environment is preferable.

In some examples according to the present disclosure, the bio-electrochemical sensor is located 0 cm, about 1 cm, about 2 cm, about 5 cm, about 10 cm, about 15 cm, about 20 cm, about 25 cm, or the distance is from any one of the distances listed above to any other of the distances listed above, from a membrane in an MBR wastewater treatment system. The distance between the bio-electrochemical sensor and the membrane may be decreased, for example when increasing the accuracy of the effects of the one or more agents on the membrane is preferable.

In some examples according to the present disclosure, the bio-electrochemical sensor is positioned in close proximity to the portion of the wastewater treatment tank where the wastewater enters the tank, for example when monitoring and/or controlling one or more agents entering the tank from upstream sources is preferable. In some examples according to the present disclosure, the bio-electrochemical sensor is positioned in close proximity to the portion of the wastewater treatment tank where the water exits the tank, for example when monitoring one or more agents that are exiting the tank is preferable. In some examples according to the present disclosure, more than one bio-electrochemical sensor is positioned within a wastewater treatment tank, for example when monitoring one or more agents at different locations within the tank is preferable. In some examples according to the present disclosure, one bio-electrochemical sensor is positioned in close proximity to the portion of the wastewater treatment tank where the wastewater enters the tank, and one bio-electrochemical sensor is positioned in close proximity to the portion of the wastewater treatment tank where the water exits the tank, for example when: (1) monitoring a change in the amount of the one or more agents in the tank; (2) monitoring the movement of the one or more agents in the tank; or (3) a combination there of, is preferable. In some examples according to the present disclosure, at least one bio-electrochemical sensor is positioned in close proximity to each of the membranes within the tank. In some examples, more than one bio-electrochemical sensor is positioned in close proximity to each one of the membranes within a tank, for example when increasing the accuracy of monitoring the effects of the one or more agents on a membrane is preferable.

The compactness of the herein described bio-electrochemical sensors refers to the orientation and space between the anode and the cathode. In some examples according to the present disclosure, the anode and cathode are configured in parallel. In some examples according to the present disclosure, at least a portion of the anode overlaps with at least a portion of the cathode. The portion of overlap may refer to portions along the length of the electrodes. In some examples according to the present disclosure, the overlapping portion of the anode and the overlapping portion of the cathode are, independently, about 10%, about 20%, about 25%, about 50%, about 75%, 100%; or the percentage is from any one of the percentages listed above to any other of the percentages listed above, of the length of the electrode or cathode. In some examples according to the present disclosure, the distance between the overlapping portions of the anode and the cathode is about 1 mm, about 2 mm, about 3 mm, about 4 mm, about 5 mm, about 6 mm, about 7 mm, about 8 mm, about 9 mm, about 10 mm; or the distance is from any one of the distances listed above to any other of the distances listed above.

In some examples according to the present disclosure, the bio-electrochemical sensor comprises a current sensor. In the context of the present disclosure, a current sensor is any sensor that measures electron flow between the anode and the cathode, and produces an electrical output. In some examples, the current sensor comprises a terminal electron acceptor in electrical communication with the cathode for receiving electrons therefrom, and a resistor in electrical communication with the electrode pair, where electrical current is measured across the resistor. In the context of the present disclosure, a resistor refers to any electrical component that impedes electrical resistance. In some examples, the resistor operates in the range of from about 1 Ohm to about 10,000 Ohms, for example, 1 Ohm, 2 Ohms, 3 Ohms, 4 Ohms, 5 Ohms, 6 Ohms, 7 Ohms, 8 Ohms, 9 Ohms, 10 Ohms, 25 Ohms, 50 Ohms, 75 Ohms, 100 Ohms, 250 Ohms, 500 Ohms, 1,000 Ohms, 2,500 Ohms, 5,000 Ohms, 7,500 Ohms, 10,000 Ohms; or the electrical resistance is between any one of the electrical resistances listed above to any other of the electrical resistances listed above. In some examples, the resistor is a low-Ohm resistor (about 5 Ohms). Measuring an electrical output across the resistor refers to measuring the change in electrical potential before and after the resistor.

As discussed above, the systems and methods described herein may control the delivery of one or more agents into the wastewater treatment system, for example, when an imbalance or deviation is measured in the system. In some examples according to the present disclosure, the one or more agents comprises at least one cleaning agent. In the context of the present disclosure, a cleaning agent is any chemical agent that is introduced into the wastewater treatment system to clean all or part of the wastewater treatment system, such as a membrane in an MBR. In some examples, the cleaning agent is sodium hypochlorite, peracetic acid, citric acid, or a combination thereof. In some examples, the cleaning agent is peracetic acid.

The herein described systems and methods may initiate, increase, decrease, or discontinue the delivery of agents into the wastewater treatment system in response to a signal produced as a result of a change in electric output when the electric output meets or exceeds a threshold. In some examples according to the present disclosure, cleaning agents may negatively impact the exo-electrogenic bacteria resulting in a decrease in metabolic activity and a decrease in measured current.

The herein described systems may comprise an electrical output analyzer, which refers to any processor in communication with the sensor and able to analyze the electrical output from the sensor and provide a signal, when appropriate, to cause an adjustment in the wastewater treatment system. In some examples according to the present disclosure, a signal is provided when the electrical output meets a threshold output, or deviates from a reference output.

In the context of the present disclosure, a threshold output is an output (such as a current measurement) at which the wastewater treatment system parameters are no longer at levels acceptable for the continuing operation or function of the wastewater treatment system. As would be known by one of skill in the art, determining what is considered an acceptable parameter level(s) for the operation or function of a wastewater treatment system will be dependent on, or determined by the specific wastewater treatment system. In some examples, the threshold current or other output may represent a deviation from a reference operating electrical output of, for example, about 5%, about 10%, about 20%, about 50%, about 100% deviation, or the percentage is from any one of the percentages listed above to any other of the percentages listed above. The reference operating output may, for example, be a baseline or steady-state current. A skilled person, such as a manufacturer or an operator, will be able to determine acceptable levels of deviation. The threshold current may be pre-determined, for example, from previous methods; known values in the art; or a value determined using alternative methods known to a skilled person. In some examples, the threshold is determined relative to the current generated from the metabolic activity of the exo-electrogenic bacteria under standard operating conditions, for example, temperature, pH, pressure, and water flow across the membrane.

In some examples according to the present disclosure, the deviation may be measured over time; and, a threshold may be set based on one or both of the deviation and time. For example, a deviation may be measured over a period of about 1 second to about 5 hours, for example, about 1 second, 2 seconds, 3 seconds, 5 seconds, 10 seconds, 20 seconds, 30 seconds, 60 seconds, 120 seconds, 240 seconds, 500 seconds, 1000 seconds, 3600 seconds, 5000 seconds, 10,000 seconds, 18,000 seconds; or the time is from any one of the times listed above to any other of the times listed above. In some examples according to the present disclosure, measurement is initiated about 10 seconds after the addition of a cleaning agent, and the wastewater treatment system is monitored for a deviation for about 1 hour thereafter. In some examples according to the present disclosure, a threshold deviation may be a deviation of greater than about 10% from the reference operating electrical output over about 2 hours from the introduction of one or more agents into the wastewater treatment system. In some examples according to the present disclosure, a deviation may be measured in less than about 15 seconds, about 10 seconds, about 5 seconds, about 1 second, or the time is from any one of the times listed above to any other of the times listed above, after the introduction of one or more agents or condition. The impact of the agent may be visualized by the operator, or signaled by a system if it has an impact on the bio-electrochemical sensor. This variation or deviation in output from the bio-electrochemical sensor may be used to discontinue or control the addition of the cleaning agent. The amount of time after the introduction of one or more agents or condition in which a change in current can be measured will depend on various factors, for example, components in the wastewater treatment system, volumetric size of the wastewater treatment system, the type and amount of exo-electrogenic bacteria, or a combination thereof.

In some examples according to the present disclosure, the herein described systems and methods may be used to adjust the amount, type, or combination thereof of cleaning agents delivered into the wastewater treatment system. In some examples, once it is determined that the measured current has reached the determined threshold, a signal is sent to a pump that controls the delivery of the cleaning agent into the wastewater treatment system, which in turn decreases or discontinues the delivery of the cleaning agent. Once it is determined that the measured current is within an acceptable range or within the threshold output, a further signal may be sent to the pump to increase or commence the delivery of the cleaning agent. In some examples, a delivered cleaning agent may be consumed by alternative chemicals in the wastewater treatment stream. Accordingly, the measured current may be a reflection of the cleaning agent remaining in the wastewater treatment system that is able to treat the membrane(s), affect the microorganisms and exo-electrogenic bacteria in the wastewater treatment system, or a combination thereof.

In some examples according to the present disclosure, the current may decrease in correlation with reduced metabolic activity of the exo-electrogenic bacteria due to the presence of chemical compounds, such as certain cleaning agents that are toxic to microbial communities. Conversely, some cleaning agents may cause an increase in the exo-electrogenic activity, for example due to selective inhibition of distinct microbial partners, increased production of volatile fatty acids, causing additional electron transfer pathways, increased mediators, increased oxidation or reduction potential, or a combination thereof. Thus, the interaction between the cleaning agent(s) and exo-electrogenic bacteria may be distinct when using each specific cleaning agent, and may require correlation to each cleaning agent or combination. In some examples according to the present disclosure, specific cleaning agents may be identified by their distinct impact on the measured current. For example, a standard curve could be developed for common cleaning agents and/or common combinations in a particular wastewater treatment system. Accordingly, the presently disclosed methods may be used to better understand the impact of specific cleaning agents on resident microbial populations. The herein described bio-electrochemical sensors, related systems and methods may be used to identify optimal concentrations of toxic cleaning agents, including identifying both low levels and high levels. In some examples according to the present disclosure, the presently disclosed bio-electrochemical sensors may be used in a method of identifying, monitoring, or a combination thereof, a particular cleaning agent in a wastewater treatment system.

In some examples according to the present disclosure, cleaning may be initiated when certain suboptimal operating conditions are reached (e.g. reduced flow across membrane, change in pressure, change in pH, etc.). In some examples according to the present disclosure, a pressure sensor is used to predict membrane clogging and initiate cleaning. In some examples according to the present disclosure, cleaning is based on time; for example, time since last cleaning, as measured in seconds, minutes, days, weeks, months or years.

In some examples according to the present disclosure, an operator affects an adjustment on the system in response to signals provided by the methods, systems, and bio-electrochemical sensors as presently disclosed. In other examples according to the present disclosure, a processor running an algorithm and in communication with the presently disclosed systems and bio-electrochemical sensors predicts imbalances on the wastewater treatment system based on the electrical output provided by the herein described systems and bio-electrochemical sensors, and adjusts the wastewater treatment system in response to the prediction. In some examples according to the present disclosure, the processor is a predictive learning machine.

The present disclosure further provides a method of monitoring the viability of microorganisms in a wastewater treatment system. Generally, the method comprises providing exo-electrogenic bacteria in the wastewater treatment system. The current generated from the metabolic activity of the exo-electrogenic bacteria is measured and compared to a reference current of a viable amount of the microorganisms. If the measured current is above or below the set threshold current, an adjustment is needed. A viable amount of the microorganisms is a sufficient amount of microorganisms for the wastewater treatment system to operate. The amount may depend on the type, size, or combination thereof of the wastewater treatment system. In some examples according to the present disclosure, the presently disclosed bio-electrochemical sensors may be used in the method of monitoring the viability of microorganisms in a wastewater treatment system.

Also provided in the present disclosure are methods and systems for controlling a pump to deliver optimal concentrations of cleaning agent(s). In some examples according to the present disclosure, the electrical output analyzer provides a signal to a controller, which in turn controls the delivery of one or more cleaning agents into the wastewater treatment system via a pump. In the context of the present disclosure, the controller is any processor in communication with the bio-electrochemical sensor that accepts a signal from the electrical output analyzer and relays the signal to a pump. In some examples according to the present disclosure, the presently disclosed bio-electrochemical sensors may be used in the methods and systems of controlling a pump to deliver optimal concentrations of cleaning agent(s).

Also provided in the present disclosure are methods and systems for controlling a valve to control the delivery of wastewater into the wastewater treatment system. In some examples according to the present disclosure, the electrical output analyzer provides a signal to a controller, which in turn controls the delivery of the wastewater into the wastewater treatment system via a valve coupled to the wastewater treatment system, for example when decreasing the one or more agents that enter the wastewater treatment system from upstream sources is preferable. In the context of the present disclosure, the valve is any device that discontinues or controls the flow of material into the wastewater treatment system. In some examples, the valve directs or redirects the flow of wastewater into a separate chamber. In some examples according to the present disclosure, the presently disclosed bio-electrochemical sensors may be used in the methods and systems of controlling a valve to control the delivery of wastewater into the wastewater treatment system.

Further provided in the present disclosure are methods and systems for correlating bio-electrochemical sensor data with pressure drop across the membranes to help accurately chemically dose membranes of wastewater treatment systems (e.g. MRB systems). In some examples according to the present disclosure, the presently disclosed systems and methods further comprise at least one pressure sensor positioned in close proximity to a membrane in an MBR system for measuring the pressure across a membrane, for example when increasing the efficiency of chemically dosing the membranes is preferable. In some examples according to the present disclosure, the presently disclosed bio-electrochemical sensors may be used in the systems and methods for correlating bio-electrochemical sensor data with a pressure drop across the membranes of wastewater treatment systems to help accurately chemically dose the membranes.

Further provided in the present disclosure are methods and systems for correlating bio-electrochemical sensor data with a decrease flow across the membranes to help accurately chemically dose the membranes of wastewater treatment systems (e.g. MRB systems). In some examples according to the present disclosure, the presently disclosed systems and methods further comprise at least one flow meter positioned in close proximity to a membrane in an MBR system for measuring the flow rate across a membrane, for example when increasing the efficiency of chemically dosing the membranes is preferable. In some examples according to the present disclosure, the presently disclosed bio-electrochemical sensors may be used in the systems and methods for correlating bio-electrochemical sensor data with a decrease flow across the membranes to help accurately chemically dose the membranes.

The present disclosure also provides for a methods and systems for correlating bio-electrochemical sensor data with pressure drop and flow across the membranes to help accurately chemically dose the membranes of wastewater treatment systems.

As noted above, the present disclosure provides a bio-electrochemical sensor for performing the above described methods, as well as for being incorporated into the above described systems. An exemplary sensor configuration is shown in FIG. 1. The sensor (100) generally comprises: an electrode pair comprising an anode (104) and a cathode (106), the anode (104) in electrical communication with the exo-electrogenic bacteria (108) for receiving electrons therefrom; a resistor (110) electrically coupled to the electrode pair, the electrical current being measured across the resistor (110); a power source (112) in electrical communication with the electrode pair for delivering voltage across the electrode pair; and a terminal electron acceptor (not shown) for receiving electrons from the cathode. Changes in electrical output may be used to optimize wastewater treatment system performance, for example, to determine optional delivery of cleaning agents to the system, or to predict which cleaning agents are present in the wastewater treatment system, etc. A change in electrical output may be measured against a set threshold to determine when an adjustment is needed.

Figure 2:
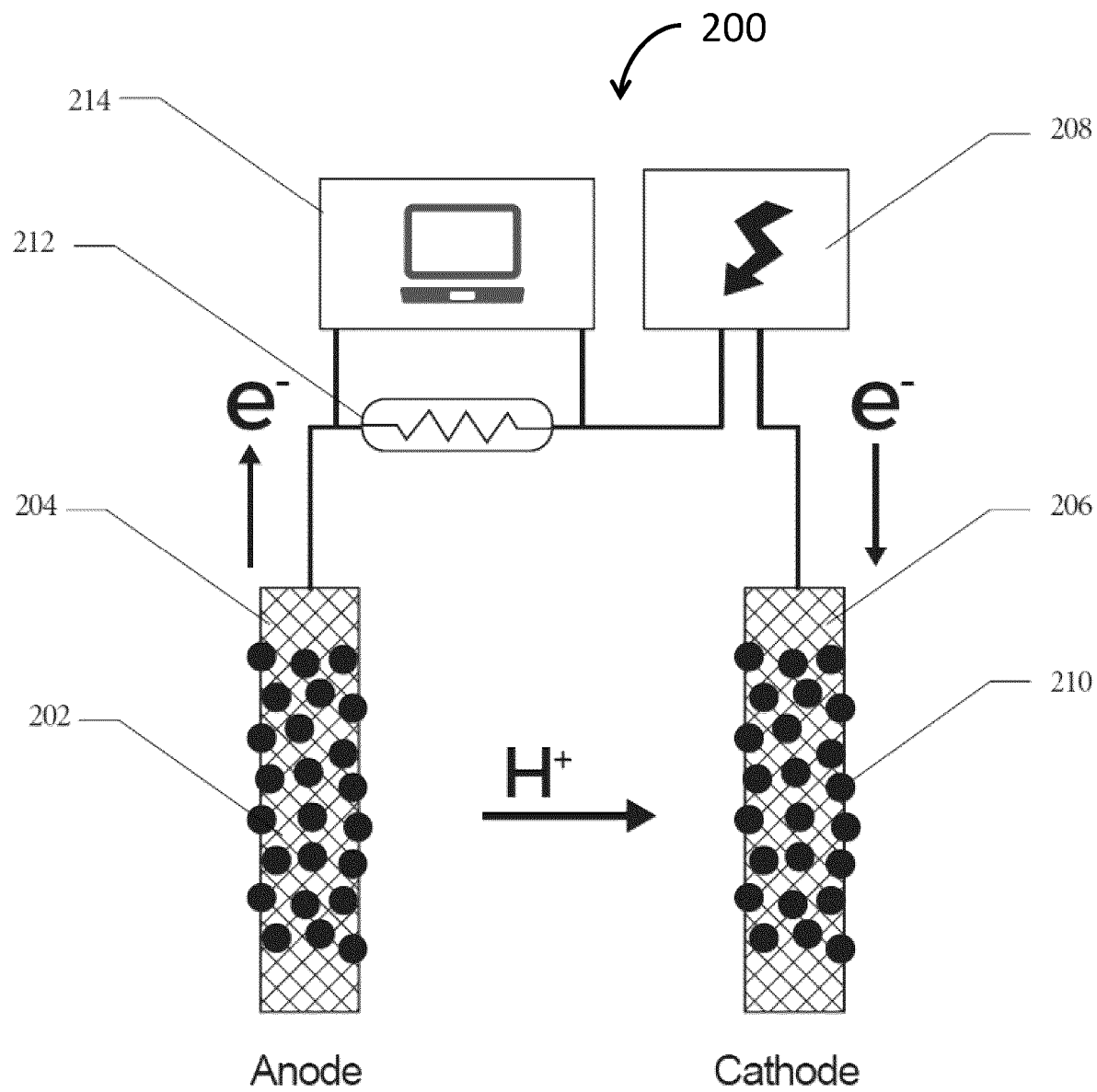
FIG. 2 is an illustration of another exemplary bio-elecrochemical sensor according to the present disclosure.

Another exemplary bio-electrochemical sensor configuration is shown in FIG. 2. The sensor (200) comprises: a support comprising a bio support material for supporting growth of exo-electrogenic bacteria (202); an electrode pair connected to the support comprising a cathode (206) and an anode (204), the anode (204) in electrical communication with the exo-electrogenic bacteria (202) for receiving electrons therefrom; a power source (208) in electrical communication with the electrode pair (204, 206) for delivering a voltage across the electrode pair (204, 206); a terminal electron acceptor (210) electrically coupled to the cathode (206) for receiving electrons from the cathode (206) and for generating an electrical output that correlates with metabolic activity of the exo-electrogenic bacteria (202); and a resistor (212) electrically coupled to the terminal electron acceptor (210; $H^+$), wherein the output is measured across the resistor using a data acquisition system or electrical output analyzer (214). Changes in electrical output may be used to optimize wastewater treatment system performance; for example, by monitoring the metabolic activity of a population of exoelectrogenic bacteria in response to one or more agents delivered to the wastewater treatment system, such that delivery of the agents can be adjusted, as needed in response to changes in the metabolic activity.

Figure 3A:
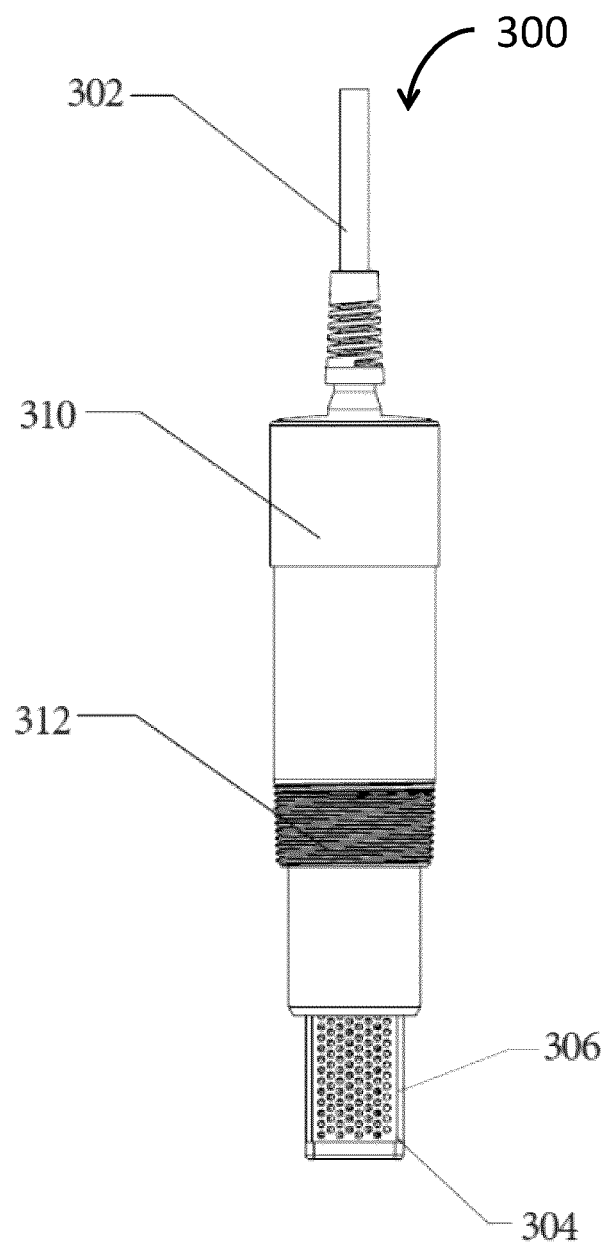
FIGS. 3A-3C are illustrations of an exemplary bio-electrochemical sensor according to the present disclosure in front elevational view (FIG. 3A), side elevation view (FIG. 3B), and bottom planar view (FIG. 3C).
Figure 3B:
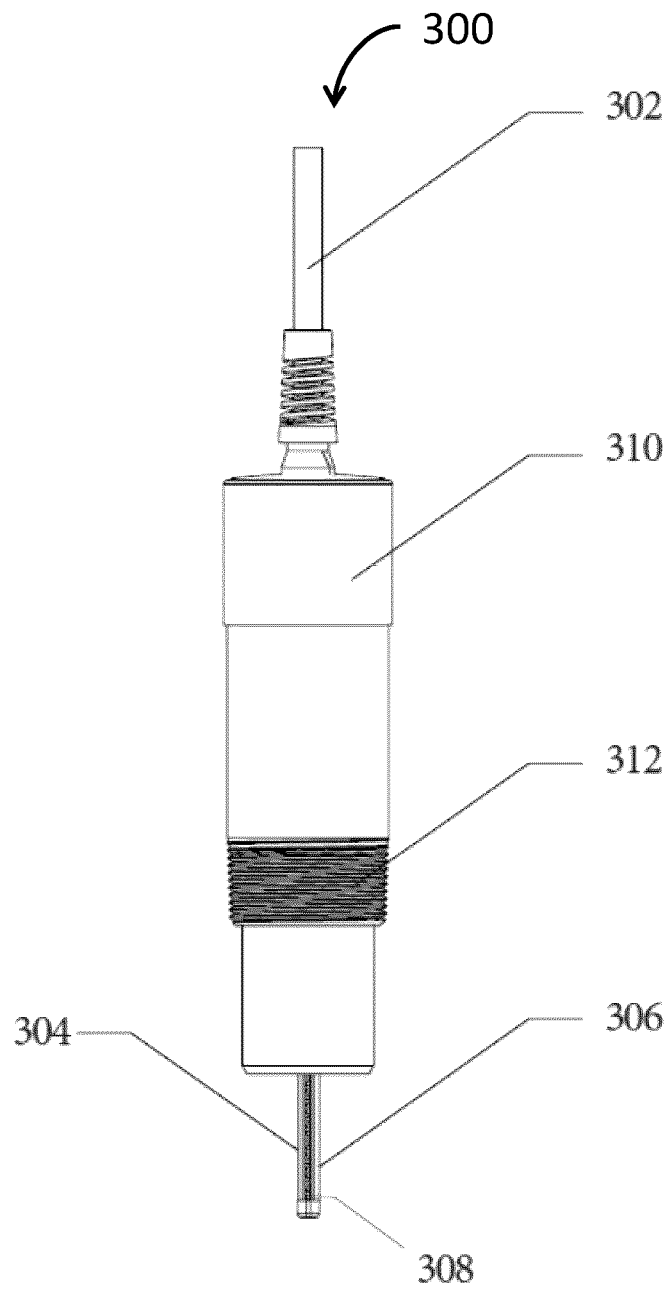
Figure 3C:
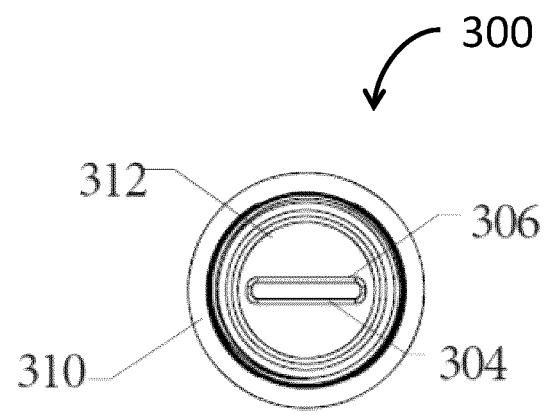

A further exemplary bio-electrochemical sensor configuration is shown in FIGS. 3A-C from various perspectives. The sensor (300), comprises a power and data cable (302) for connecting the sensor to a power source and electrical output analyzer (not shown); an electrode pair comprising a cathode (306) and anode (304), wherein the anode (304) is in electrical communication with exo-electrogenic bacteria (not shown), coupled to a bio support (308), for receiving electrons therefrom; a sealed probe body (310) for housing the electrode pair; and an installation thread (312) for connecting the sensor to various fittings, for example, an in-line T fitting; see FIGS. 6A-B). As more clearly depicted in FIG. 3B, the cathode (306) and the anode (304) are configured in parallel, and at least a portion of the anode (304) overlaps with at least a portion of the cathode (306). In some examples, the distance between the overlapping portions is about 3 mm.

Figure 4:
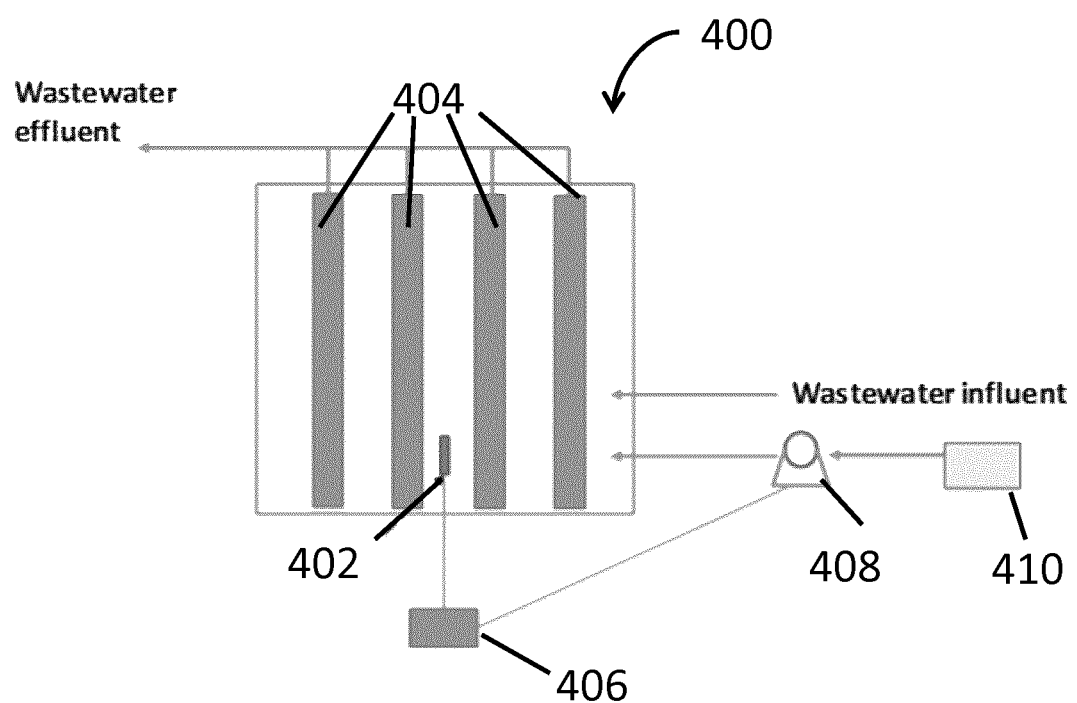
FIG. 4 is an illustration of an exemplary bio-electrochemical sensor according to the present disclosure used in a platform to control the delivery of cleaning agents to a membrane based wastewater treatment system.

In some examples according to the present disclosure, the bio-electrochemical sensor according to the present disclosure may be used in a wastewater treatment system to control the delivery of one or more cleaning agents into the wastewater treatment system, as illustrated in FIG. 4. In the membrane based wastewater treatment system (400), the bio-electrochemical sensor (402) is located adjacent to, or in close proximity to, the membrane surface (404) within the membrane based wastewater treatment system (400); and, is in communication with a controller, such as a sensor control panel (406). When the measured output of the bio-electrochemical sensor (402) deviates beyond a threshold, the control panel (406) sends a signal to a pump (408), which in turn decreases or stops the delivery of the cleaning agent (410). When the measured output no longer exceeds the threshold, the control panel (406) may send a further signal to the pump (408) to increase or commence the delivery of the cleaning agent (410). In some examples, the next cleaning may be triggered by time, for example, time since last cleaning.

Figure 5:
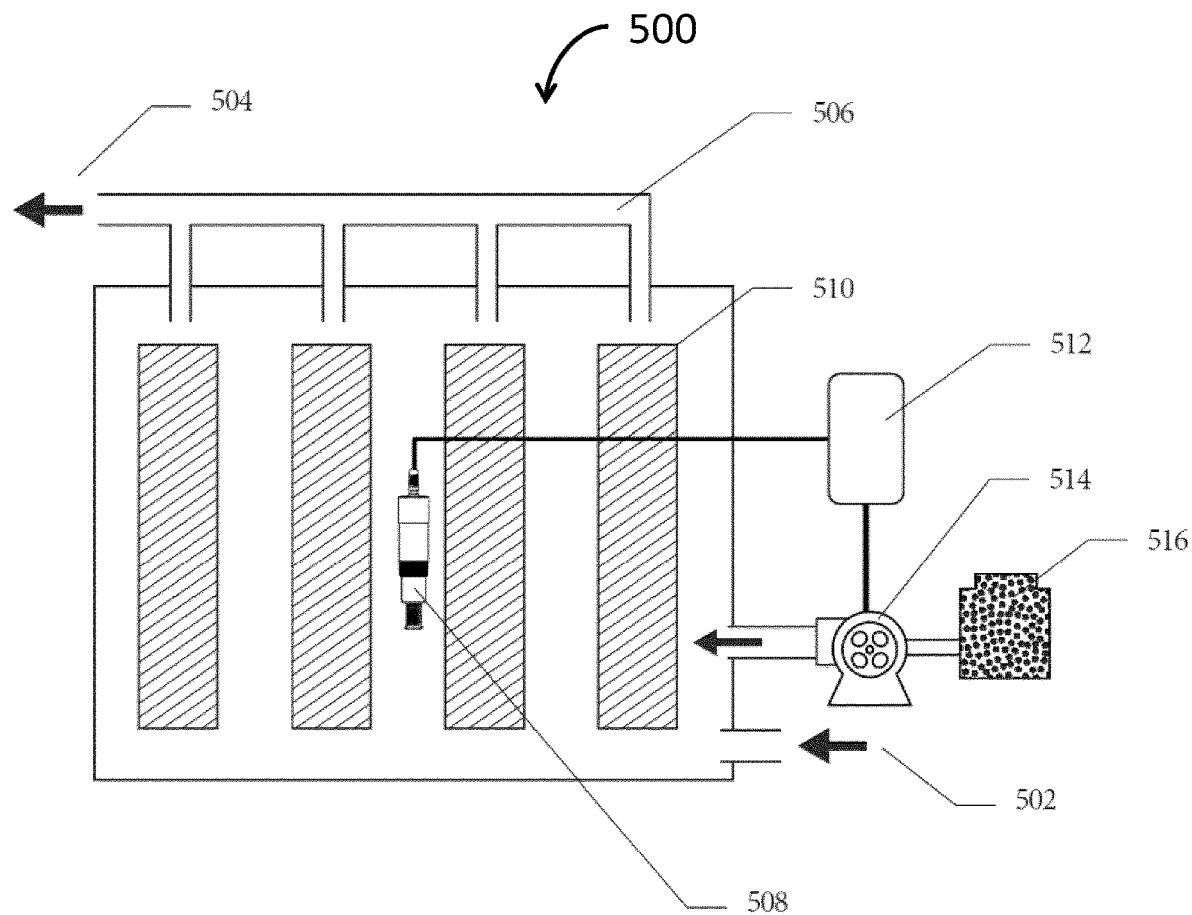
FIG. 5 is an illustration of the exemplary bio-electrochemical sensor shown in FIGS. 3A-C used in a platform to control the delivery of cleaning agents to a membrane based wastewater treatment system.

In some examples, the bio-electrochemical sensor according to the present disclosure may be used in a membrane-based anaerobic suspended growth digestion system of a wastewater treatment system to monitor, or control the delivery of one or more cleaning agents in the wastewater treatment system, as illustrated in FIG. 5. The membrane-based anaerobic suspended growth digestion system (500) comprises a wastewater influent (502) and effluent (504) and appropriate effluent piping (506); and, a bio-electrochemical sensor as illustrated in FIGS. 3A-C (508) located adjacent to, or in close proximity to, the membrane surfaces (510), the sensor (508) in communication with a controller (512), such as a sensor control panel. When a measured output of the bio-electrochemical sensor (508) deviates beyond a threshold, the control panel (512) sends a signal to a pump (514), which in turn decreases or stops the delivery of cleaning agent (516). When the measured output no longer exceeds the threshold, the control panel (512) may send a further signal to the pump (514) to increase or commence delivery of cleaning agent (516). In some examples, the next cleaning may be triggered by a predetermined time; a change in wastewater pressure across a membrane(s); or, a change in wastewater flow rate across a membrane(s).

Figure 6A:
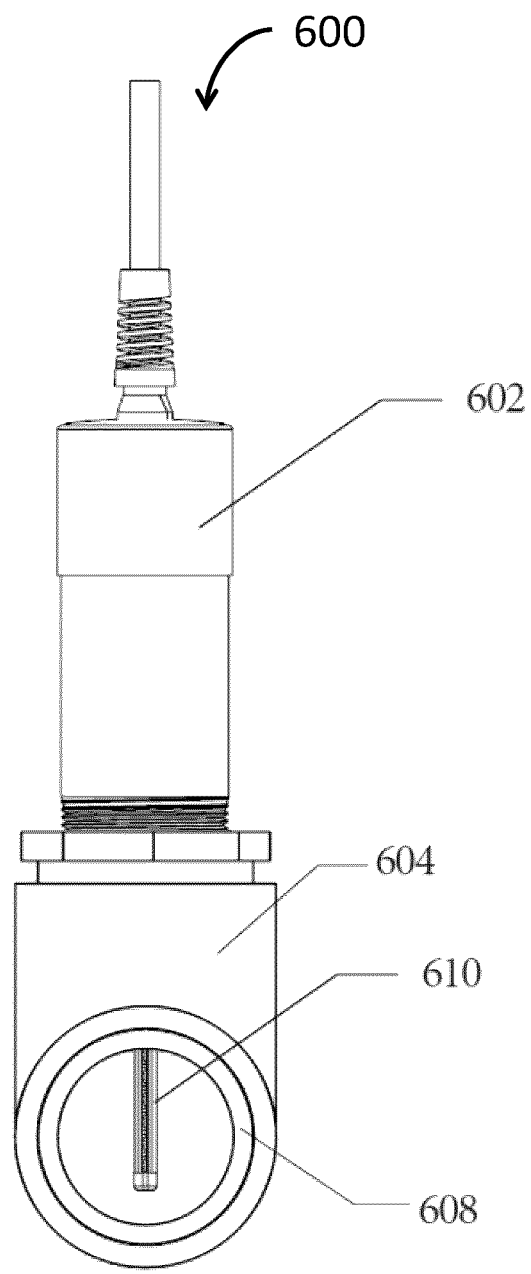
FIGS. 6A-B are illustrations of the exemplary bio-electrochemical sensor shown in FIGS. 3A-C associated with an in-line T fitting in front elevation view (FIG. 6A) and side elevation view (FIG. 6B).
Figure 6B:
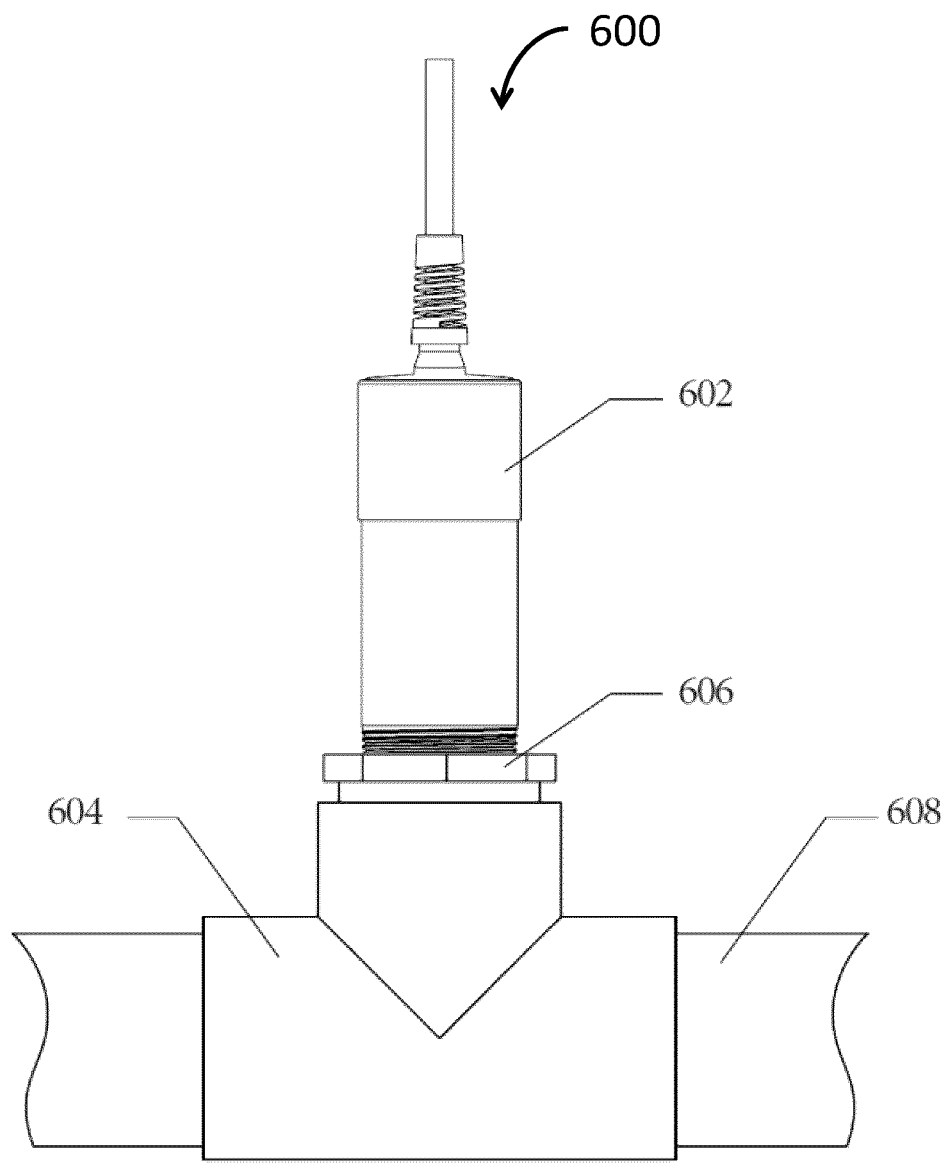

In some examples according to the present disclosure, the bio-electrochemical sensor may be placed in a recirculating loop or in an external tank that is hydraulically connected to the wastewater treatment system. FIGS. 6A-B depict an example of a bypass fitting (600) in a recirculating loop comprising a bio-electrochemical sensor as illustrated in FIGS. 3A-C (602) coupled to an in-line T fitting (604) via threaded connector (606), wherein T fitting (604) is coupled to standard piping (608) in communication with the wastewater treatment system (not shown). As shown more clearly in FIG. 6A, electrode pair (610) of the bio-electrochemical sensor (602) is disposed within the standard piping (608) via T fitting (604) to allow the electrode pair (610) to be exposed to, for example, wastewater of a wastewater treatment system; and thus, the bio-electrochemical sensor (602) facilitates monitoring, or controlling delivery of, one or more agents in said wastewater treatment system by monitoring the metabolic activity of the exo-electrogenic bacteria and providing an electrical output that correlates with the metabolic activity.

In some examples according to the present disclosure, the methods and sensors according to the present disclosure may be used to better understand the concentration of cleaning agents that the microorganisms in the wastewater treatment system are exposed to, for example, by measuring the amount of cleaning agent delivered into the wastewater treatment system while taking into account concentration loss of the cleaning agent due to additional compounds in the wastewater that absorb, consume, attack, or a combination thereof, the cleaning agent. The concentrations of the cleaning agents would be calculated or estimated.

References to other documents are made throughout this disclosure. Such documents are incorporated herein by reference in their entirety.

EXAMPLES

Figure 7:
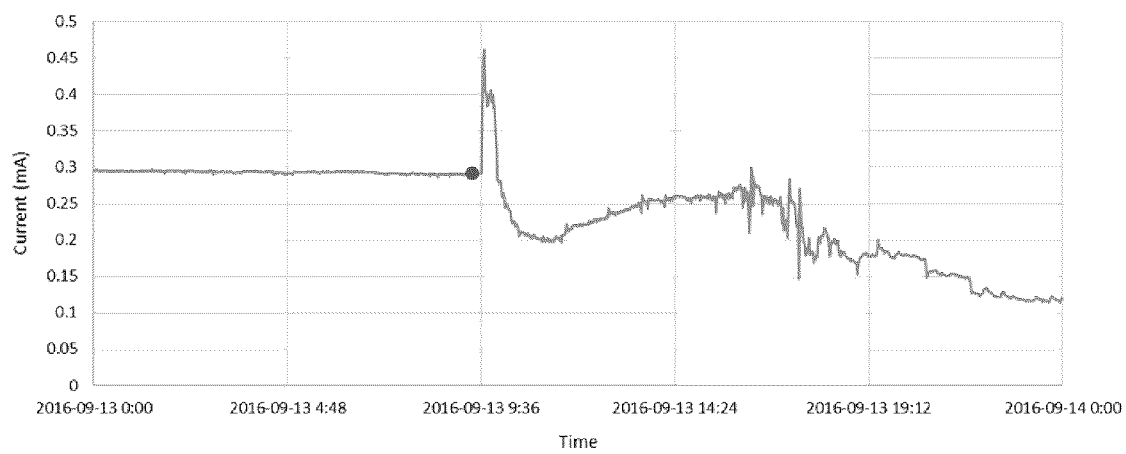
FIG. 7 is a graph illustrating a bio-electrogenic response to a defined concentration of sodium hyperchlorite (50 mg/L) that was added to a wastewater treatment system (addition signified with dot).

Example 1—Measuring a Bio-Electrogenic Response to a Defined Concentration of Sodium Hypochlorite As shown in FIG. 7, about 50 mg/L of sodium hypochlorite was added to a wastewater treatment system (addition signified with dot). Before the toxicity study commenced, sensors were inoculated with a community of microorganisms. Bio-electrochemical sensors (BES) were placed in an anaerobic environment submerged in synthetic wastewater and agitated using a shaker table. This system was mixed weekly to replace the synthetic wastewater in air tight containers holding the BES. Replacement of the synthetic wastewater effluent was replaced by: opening the containers, taking about 10 mL of the effluent and mixing it with a new feed as an inoculation, removing remaining week-old effluent, pouring in a same volume of new inoculated feed in the containers, and then replacing the container's lid. This inoculation process was performed over a three-week period in order to grow a biofilm which produced steady state current. During the first week of inoculation, the current produced by the biofilm increased over the inoculation period until it reached a steady state.

Once a steady state was reached and a dosage concentration of a selected chemical was determined, a hole was drilled in the lid of each BES probe's container, which was used for the toxicity study. The selected chemical was added through this hole using 1 mL needle syringes, and the hole was immediately plugged to prevent any extra oxygen from entering the container. Output data was monitored and recorded to better understand changes in microbial activity.

For this study, solutions of peracetic acid (a common wastewater disinfectant) and household bleach (6% sodium hypochlorite disinfectant) were used for testing impacts of different strengths of toxicity on the current production of the biofilm growing on the BES. All chemical solutions were made with laboratory-grade deionized (DO) water Bleach Shock Testing A 6% sodium hypochlorite (NaOCL) bleach solution (Lavo Pro™ 6 Commercial Bleach) was used as a stock solution for a bleach shock testing. This solution was diluted to concentrations of 0.5 mg/L, 1 mg/L, 1.5 mg/L, 2 mg/L, 5 mg/L, 10 mg/L, 15 mg/L and 20 mg/L, and 50 mg/L. These concentrations were tested on BES that had achieved a steady state for greater than a 24 h period. Bleach solution was administered to the respective BES using syringe needles, and were dispensed through a hole in the BES lid.

Figure 8:
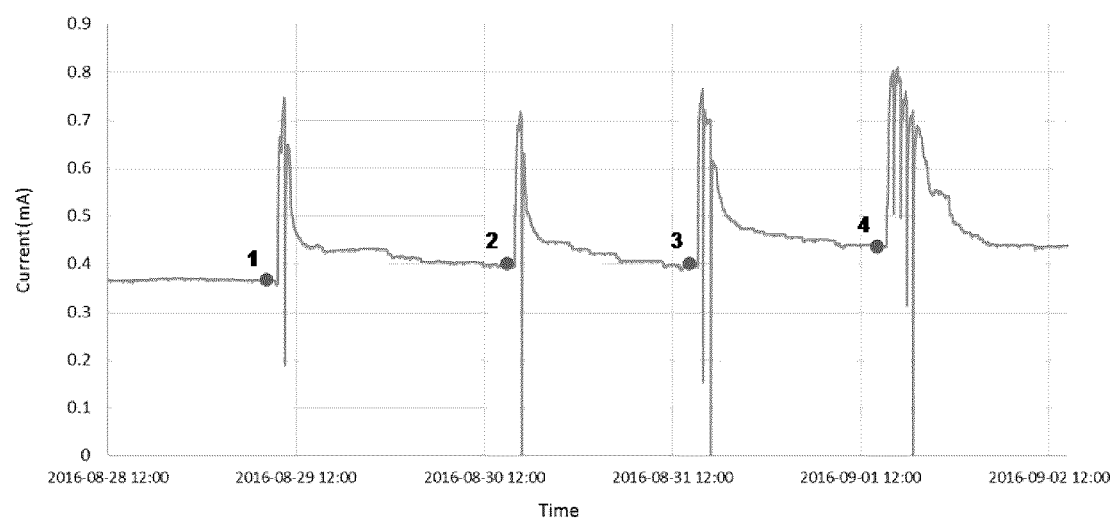
FIG. 8 is a graph illustrating a bio-electrogenic response to defined dosing concentrations of peracetic acid at (1) 5 mg/L, (2) 10 mg/L, (3) 20 mg/L and (4) 50 mg/L to a wastewater treatment system at times signified by dots.

Example 2—Measuring a Bio-Electrogenic Response to Defined Dosing Concentrations of Peracetic Acid As shown in FIG. 8, about (1) 5 mg/L, (2) 10 mg/L, (3) 20 mg/L and (4) 50 mg/L of peracetic acid was added to a wastewater treatment system at times signified by dots.

Peracetic Acid Testing

A peracetic acid solution (Sigma Aldrich) at a concentration percentage of 39% peracetic acid, 46% acetic acid, and ≤6% hydrogen peroxide ($H_2O_2$) was used for a chemical shock testing of the laboratory BES. In this trial, four concentrations were used: 5 mg/L, 10 mg/L, 20 mg/L, and 50 mg/L. Dosing was performed between roughly 24 hour periods to allow for a relative steady state to be achieved following each dosing.

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A system for monitoring one or more agents in a biological wastewater treatment system, the system comprising:
a bio-electrochemical sensor for monitoring metabolic activity of a population of exo-electrogenic bacteria and providing an electrical output corresponding with the metabolic activity, the bio-electrochemical sensor comprising an electrode pair and a power source for delivering a voltage across the electrode pair; and
an electrical output analyzer for analyzing the electrical output and correlating the electrical output with the one or more agents in the wastewater treatment system,
wherein the one or more agents comprise at least one cleaning agent, and
wherein the biological wastewater treatment system is an anaerobic digestion system, and the bio-electrochemical sensor is located within the anaerobic digestion system.

2. The system of claim 1, wherein the anaerobic digestion system incorporates a treatment process comprising a membrane.

3. The system of claim 1, wherein the at least one cleaning agent comprises a membrane cleaning agent, sodium hypochlorite, peracetic acid, citric acid, or a combination thereof.

4. The system of claim 1, further comprising a controller in communication with the electrical output analyzer for initiating a cleaning process in response to a trigger.

5. The system of claim 4, wherein the trigger is a pre-determined time.

6. The system of claim 4, which permits real time adjustments in the delivery of the one or more agents.

7. A method of monitoring one or more agents in a biological wastewater treatment system, the method comprising:
applying power to a bio-electrochemical sensor;
measuring an electrical output of the bio-electrochemical sensor and correlating the output with metabolic activity of exo-electrogenic bacteria present in the wastewater treatment system; and
correlating the electrical output with the one or more agents in the wastewater treatment system,
wherein the one or more agents comprise at least one cleaning agent, and
wherein the biological wastewater treatment system is an anaerobic digestion system, and the step of measuring the electrical output is measured within the anaerobic digestion system.

8. The method of claim 7, which is incorporated in a method of cleaning a membrane associated with the wastewater treatment system.

9. The method of claim 8, further comprising initiating a membrane cleaning cycle in response to a trigger.

10. The method of claim 9, wherein the trigger is a pre-determined time.

11. The method of claim 7, further comprising:
delivering the one or more agents into the system;
monitoring a change in the electrical output in response to the delivery of the one or more agents; and
adjusting the delivery of the one or more agents in response to a change in the electrical output.

12. The method of claim 11, wherein real time adjustments in the delivery of the one or more agents can be made throughout a cleaning process in response to changes in the electrical output.

13. The method of claim 11, which is incorporated in a method of cleaning a membrane associated with the wastewater treatment system.

14. The method of claim 11, which comprises adjusting the delivery of the one or more agents in response to a change in electrical output beyond a threshold.

15. The method of claim 14, wherein the change in electrical output is monitored over a period of time.

16. The method of claim 7, wherein the at least one cleaning agent comprises a membrane cleaning agent, sodium hypochlorite, peracetic acid, citric acid, or a combination thereof.

17. The system of claim 4, wherein the electrical output analyzer provides a signal to the controller for controlling delivery of one or more agents in response to the signal.

18. The system of claim 17, further comprising: a pump operably coupled to the controller for controlling the delivery of the one or more agents in response to the signal; or a valve operably coupled to the controller for controlling the delivery of wastewater into the wastewater treatment system in response to the signal.

19. A method of monitoring one or more agents in a biological wastewater treatment system, the method comprising:
- applying power to a bio-electrochemical sensor;
- measuring an electrical output of the bio-electrochemical sensor and correlating the output with metabolic activity of exo-electrogenic bacteria present in the wastewater treatment system;
- correlating the electrical output with the one or more agents in the wastewater treatment system,
- delivering the one or more agents into the wastewater treatment system;
- monitoring a change in the electrical output in response to the delivery of the one or more agents; and
- adjusting the delivery of the one or more agents in response to a change in the electrical output,
- wherein the one or more agents comprise at least one cleaning agent.

* * * * *